(12) United States Patent
Auret et al.

(10) Patent No.: US 8,746,968 B2
(45) Date of Patent: Jun. 10, 2014

(54) MICROSENSOR PRODUCED IN MICROSYSTEM TECHNOLOGIES FOR THE MEASUREMENT AND/OR DETECTION OF FOULING

(75) Inventors: Laurent Auret, Nailloux (FR); Frederic Flourens, Toulouse (FR); Luc Fillaudeau, Castanet-Tolosan (FR)

(73) Assignee: Neosens, Labege (FR)

( * ) Notice: Subject to any disclaimer, the term of this patent is extended or adjusted under 35 U.S.C. 154(b) by 336 days.

(21) Appl. No.: 13/144,636

(22) PCT Filed: Jan. 19, 2010

(86) PCT No.: PCT/FR2010/050080
§ 371 (c)(1),
(2), (4) Date: Jul. 14, 2011

(87) PCT Pub. No.: WO2010/082006
PCT Pub. Date: Jul. 22, 2010

(65) Prior Publication Data
US 2011/0274138 A1 Nov. 10, 2011

(30) Foreign Application Priority Data
Jan. 19, 2009 (FR) ...................................... 09 50314

(51) Int. Cl.
*G01K 1/00* (2006.01)
*G01N 25/18* (2006.01)
*G01N 17/00* (2006.01)

(52) U.S. Cl.
CPC ................................... *G01N 17/008* (2013.01); *G01N 25/18* (2013.01)
USPC ........... 374/45; 374/4; 374/7; 374/29; 374/44

(58) Field of Classification Search
USPC ......... 374/4–7, 29, 100, 101, 141, 43–45, 57, 374/208
See application file for complete search history.

(56) References Cited

U.S. PATENT DOCUMENTS 3,913,378 A * 10/1975 Hausler .............................. 374/7
4,138,878 A * 2/1979 Holmes et al. ..................... 374/7

(Continued)

FOREIGN PATENT DOCUMENTS

FR 2 788 600 A1 7/2000
FR 2 897 930 A1 8/2007

(Continued)

OTHER PUBLICATIONS

International Search Report, dated Apr. 28, 2010, from corresponding PCT application.

*Primary Examiner* — Gail Verbitsky
(74) *Attorney, Agent, or Firm* — Young & Thompson

(57) ABSTRACT

A sensor (10; 34) for measuring and/or detecting fouling that forms directly or indirectly on a so-called front surface of the sensor, includes the following in the form of a plurality of superimposed layers: —at least one heating element (14) that is able to diffuse, on command, a homogenous, monitored heat flow whose heat output is less than 200 mW, —a heat insulator (11) located on the side opposite the front surface of the sensor to prevent dissipation of the heat flow from the opposite side, —at least one temperature measuring element (16) that is placed in the homogenous heat flow diffused by the at least one heating element and that offers a precision of temperature measurement of better than 0.1° C., and —a substrate (12; 42) on which the layers of the at least one heating element and at least one temperature measuring element are connected.

22 Claims, 7 Drawing Sheets

(56) References Cited

U.S. PATENT DOCUMENTS

| | | | |
|---|---|---|---|
| 4,744,246 A * | 5/1988 | Busta | 73/204.26 |
| RE33,346 E | 9/1990 | Knudsen et al. | |
| 5,399,017 A * | 3/1995 | Droege | 374/7 |
| 5,460,041 A * | 10/1995 | Andes et al. | 73/335.08 |
| 6,238,085 B1 * | 5/2001 | Higashi et al. | 374/10 |
| 6,762,672 B2 * | 7/2004 | Taguchi et al. | 338/25 |
| 7,077,563 B2 * | 7/2006 | Xiao et al. | 374/29 |
| 2005/0105583 A1 * | 5/2005 | Xiao et al. | 374/29 |
| 2007/0025413 A1 * | 2/2007 | Hays et al. | 374/7 |
| 2008/0014615 A1 | 1/2008 | Sarofim et al. | |
| 2008/0026430 A1 | 1/2008 | Sarofim et al. | |
| 2009/0000764 A1 | 1/2009 | Tochon et al. | |

FOREIGN PATENT DOCUMENTS

| | | |
|---|---|---|
| JP | 60245023 A * | 12/1985 |
| JP | 02269923 A * | 11/1990 |

* cited by examiner

MICROSENSOR PRODUCED IN MICROSYSTEM TECHNOLOGIES FOR THE MEASUREMENT AND/OR DETECTION OF FOULING

FIELD OF THE INVENTION

The invention relates to a sensor and a system for measuring or detecting the fouling of a reactor or a pipe containing a fluid.

BACKGROUND OF THE INVENTION

On industrial sites, there are different types of installations in which fluids of various types circulate.

These installations comprise pipes in which fluids circulate and can likewise comprise reactors such as, for example, heat exchangers.

In this exact case, the fouling of such installations can have adverse effects to the degree it is capable of affecting the performances of the installations (for example, the efficiency of an industrial process).

Moreover, when fouling forms on the inside wall of a pipe or a reactor, it should be promptly cleaned.

However, it is necessary that this fouling be continuously detectable by the operators or the maintenance personnel of the installation in order to be able to assess, within the framework of preventive maintenance, the best time for cleaning.

For whatever reason, the fouling irregularly causes a shutdown of the installation during a sometimes indeterminate interval; this has serious adverse effects on the progression of the industrial process.

These interventions can represent tedious tasks for personnel, the more so if the fouling has only been detected belatedly and if its thickness is too great.

This removal of fouling has a not inconsiderable economic cost since the cost of a temporary shutdown of operation should be included in the cost of maintenance operations.

It should likewise be noted that as the heat exchangers become fouled, there is a progressive loss of efficiency before a potential shutdown of operation of the installation or the part of the installation comprising these exchangers.

Moreover, in hot water sanitation networks and in open industrial air-cooled towers, bacteria can develop within the network and the cooling circuit.

Likewise, a risk of contamination by Legionnaire's disease can be envisioned.

Currently, there should be regular monitoring of the installation by anticipating points of attack in the pipes or in the reactors in which the fluids that can cause fouling are circulating.

These points of attack likewise allow the taking of samples, and then the laboratory analysis of said samples to obtain either a measurement of fouling or an analysis of the type of fouling that has formed (type, composition . . . ).

On certain industrial sites, to measure the thickness of the layer of fouling that has formed within the walls of a pipe or a reactor, methods are used that require measurement of the loss of load that is produced between two points that are spaced in the direction of fluid flow. Likewise, methods that measure the temperature differences between these points can be used.

These latter measurements, however, present genuine problems to the degree in which:

They do not allow local information to be obtained,
They lack reactivity, but likewise sensitivity and extent of the measurement range.

Document FR 2 885 694 discloses a method for measuring the fouling in a reactor or a pipe that uses two temperature probes.

More particularly, these two probes are introduced into a pipe respectively based on two points of attack, and one of these probes measures the temperature of the fluid while the other probe measures the temperature of the wall of a heat generator.

According to this method, the point is first of all to obtain a temperature difference between the wall temperature and the fluid temperature that is as near zero as possible. Then, the heat generator emits a heat flow while the temperature deviation between the wall temperature and that of the fluid is measured over time, the state of fouling of the reactor being determined based on the measurement of this temperature deviation.

This method and the associated system, however, have certain defects that limit their use in an industrial environment.

In particular, the presence of two points of physical attack on one pipe or a reactor always constitutes an installation constraint for a manufacturer, accompanied by a not inconsiderable cost.

Moreover, two temperature probes, even if they are of the same type, always have a certain drift of operation relative to one another due to, for example, variances that arise during their manufacture.

Because of these drifts, the two probes do not have the same behavior relative to one another vis-a-vis the same temperature of the environment into which they are immersed.

Moreover, the temperature probe that is used as a reference (the one that measures the fluid temperature) can itself become fouled; this introduces an additional drift relative to the other temperature probe.

Due likewise to the kinetic (or dynamic) differences of responses between the two temperature probes, a temperature deviation between the two probes can then be noted, whereas theoretically such a temperature deviation should not arise.

Then, the method used in the aforementioned document dictates the complete absence of variation of the temperature of the fluid into which the two separate temperature measuring elements are immersed. This is because this significantly reduces the range of applications to the degree in which most industrial processes and/or water treatment processes continuously modify and perturb the average temperature of the environment.

Finally, the method used, by imposing initial conditions, at the same time requires a posteriori processing of the recorded data as well as systematic verification of the conditions before any use. Thus, this makes this method useless for continuous applications or for long-term operation (24 h/24). At best, the access to the temperature deviation (thermal drift) can be observed over the anticipated and programmed measurement period.

The defects that were just cited can thus lead to faulty measurements of fouling and thus to a lack of reliability of the method used. Moreover, as a result of the operating mode and constituent elements of the physical device, the number of possible applications is limited.

SUMMARY OF THE INVENTION

The applicant has realized that it would be advantageous to be able to have a new sensor for determination of fouling with a simplified concept that provides reliable measurements over time.

Thus, the object of this invention is a microsensor for measurement or detection of fouling, able to be implemented according to manufacturing technologies of microelectronics (ex.: microsystem technologies). More particularly, the object of the invention is a sensor for measuring and/or detecting fouling that forms directly or indirectly on a so-called front surface of the sensor, characterized in that it comprises the following in the form of a plurality of superimposed layers:

At least one heating element that is able to diffuse, on command, a homogenous, monitored heat flow whose heat output is essentially less than 200 mW, A heat insulator located on the side opposite the front surface of the sensor for preventing dissipation of the heat flow from said opposite side, At least one temperature measuring element that is placed in the homogenous heat flow diffused by said at least one heating element and that offers a precision of temperature measurement of better than 0.1° C., A substrate on which the layers of said at least one heating element and at least one temperature measuring element are connected.

A sensor whose heating element or elements generate(s) a weak heat output, for example less than or equal to 200 mW (preferably less than 100 mW, and, for example, between 1 and 50 mW) and whose temperature measuring element or elements placed in the homogenous part of the heat flow (in the heart of the flow, i.e., as far as possible from the edges of the heating element or elements to avoid edge effects) offer high precision, for example better than 0.1° C. (preferably better than 0.01° C., and, for example, between 0.005 and 0.01° C.), is especially advantageous to the degree in which it is very sensitive, very reactive and very reliable.

The characteristics of the constituent elements of this sensor that were enumerated above are linked to the fact that this sensor has very small dimensions (microsystem sensor). It can be manufactured by, for example, manufacturing technologies used in microelectronics and consisting in implementing the operating elements in the form of layers deposited on top of one another on a substrate or on either of its sides according to the desired arrangement.

The use of collective manufacturing technologies of microelectronics (MEMS) makes it possible to manufacture, for example, on a silicon disk or "wafer," a large number of sensors, especially from several hundred to several thousand. Thus, reproducibility is ensured at the same time between two manufacturing series, but equally within the same manufacturing series. The sensors or components obtained are thus identical and have the same characteristics.

The sensors that are thus manufactured in series are therefore more reliable in their operation and less difficult to produce.

Moreover, in such a sensor comprising several layers of operating elements, these elements are especially close to one another and therefore have reduced dimensions of roughly one micrometer.

For this reason, the power consumption of the elements taken separately and of the sensor as a whole is greatly reduced.

By comparison with a sensor structure, the same operating elements are used again, but would not be implemented in microsystem technology:

The microsensor is more reactive to the heat flow diffused by the heating element or elements because the heat losses are reduced;

The measuring element or elements are much more sensitive in the miniaturized sensor (for example one hundred times more sensitive);

The microsystem sensor has greater sensitivity to the measurement of the thickness of a fouling layer (for example of roughly several µm instead of several hundred µm).

Moreover, to the degree to which the sensor is very sensitive, the heat flow diffused by the heating element or elements can be greatly reduced, and it is therefore evacuated very easily by the medium in which the sensor is placed.

Thus, when the sensor is placed in a fluid or in contact with a fluid, the flow rate of the latter can be very weak, i.e., zero, and the heat flow generated by the sensor will nevertheless be satisfactorily dissipated by the fluid.

Other manufacturing technologies can be used (serigraphy, nanotechnologies, . . . ) to produce a microsensor and to obtain the same or similar advantages.

It should be noted that the sensor according to the invention is able to determine especially effectively the fouling formed on the outside surface of the latter when it is placed in a fluid or in contact with a fluid.

"Determination" of the fouling is defined as the measurement of a thickness of a layer of fouling that is formed on the sensor and/or the detection of a layer of fouling in the course of formation.

The measurement of temperature is local and not global due to the small dimensions of the measuring element, and the temperature measuring element measures the temperature of the site at which it is located.

It should be noted that such a sensor offers greater reactivity when the temperature measuring element is directly in contact with the fluid since there is no heat resistance due to the interface between the temperature measuring element and the fluid.

The sensor is thus faster and more sensitive than in the presence of the interface.

Moreover, the heating element or elements dissipate(s) a very weak heat output in order not to heat the fluid or to induce a wall temperature increase that is able to induce formation of fouling (scale . . . ).

Thus, fouling phenomena occurring naturally and not induced by the measurement device are measured.

Moreover, this low heat output is thus naturally evacuated into the fluid; this allows the sensor to be used in a stagnant medium or during interruption of the fluid circulation.

However, the heat output must be great enough that the temperature measuring element can deliver a useful signal.

It should be noted that this sensor works with a single—or with several—temperature measuring element(s).

Moreover, the sensor according to the invention can continuously provide measurements in real time, whatever the development of the conditions of the measurement medium (uncontrolled fluid temperature).

To implement this measurement and/or detection function, the sensor is part of a system that comprises means for supplying energy to the operating elements of the sensor and means of processing of the data provided by these elements. The system, moreover, optionally comprises means of display of the results (example: curve of measurement of the temperature measured as a function of time, curve of the thickness of fouling as a function of time . . . ) and/or means for remote transmission of information relating to quantitative data (temperature, thickness, . . . ) and/or qualitative data (presence or absence of fouling . . . ).

According to one characteristic, the sensor according to the invention is part of a system that is designed to measure and/or to detect the fouling that has formed or that is being formed within a container that contains a fluid. Such a container is, for example, a reactor or a pipe routing a fluid. It should be noted that the level of fouling is measured and/or detected continuously and more or less in real time, whatever the development of the conditions of the measurement medium (for example, uncontrolled fluid temperature).

The measurements are reliable over time due to the sensor according to the invention.

According to one characteristic, said at least one temperature measuring element has a surface whose size is at least essentially less than 2% of that of the surface of said at least one heating element.

This ratio of relative dimensions ensures reliability, sensitivity and reactivity of the sensor. The surface ratio can even be less than 1%.

It should be noted that the size of the surface that matters in the heating element is that of the active zone (heating zone) and not the total size including that of the inactive zone (no-heating zone, for example peripheral zone).

According to one characteristic, the active surface of said at least one heating element has a size that is less than or equal to 25 mm$^2$.

This size is relatively reduced relative to the heating elements used in sensors of the prior art.

According to one characteristic, the surface of said at least one temperature measuring element has a size that is less than or equal to 0.49 mm$^2$.

The size of this measuring element imparts to the latter dimensions that have been especially reduced and that allow it to measure a local and nonglobal wall temperature and offers the possibility of the sensor's being especially reactive.

According to one characteristic, said at least one heating element and said at least one temperature measuring element are produced in the form of resistive tracks or lines.

These resistive tracks or lines are metal deposits made on a substrate or on a layer deposited beforehand on the substrate.

These tracks are configured according to a more or less complex shape in order to obtain the desired physical characteristic or characteristics (for example obtaining a given heat flow that is as homogeneous as possible).

These tracks are, for example, arranged in such a way as to form one or more meanders located on the substrate or on the layer that can be concentrically arranged, for example.

These different arrangements allow implementation of one or more heating elements or one or more temperature measuring elements in microsystem technology by optimizing the available surface.

It should be noted that the thickness of the resistive lines or tracks can be adjusted in microsystem technology to obtain the desired properties, and, for example, for the heating element or elements to modify the heat output of the sensor.

Likewise, by modifying the thickness of the constituent metallic deposit of resistive lines or tracks, the operating characteristics of the temperature measuring element or elements such as, for example, the sensitivity and/or dynamics of response can be varied.

It should be noted, moreover, that the sensor can comprise intermediate electrical insulating layers between the different operating layers.

This or these intermediate layer(s) likewise allow the surface of the layer to be leveled to facilitate the final deposition of an upper layer or else the contact with another element.

According to one characteristic, said at least one heating element and said at least one temperature measuring element are, for example, each platinum resistors.

The heating and temperature measuring elements made in this way are especially effective.

According to one characteristic, the substrate has first and second opposite surfaces, the heat insulator facing the first surface whereas the layer of said at least one heating element is facing the second surface, the layer of said at least one temperature measuring element being superimposed on the layer of said at least one heating element.

This arrangement thus makes it possible to obtain a sensor whose operating layers of the heating element and temperature measuring element are located on the same side of the substrate on top of one another.

According to one alternate characteristic, the substrate has first and second opposite surfaces, the heat insulator facing the first surface, the layer of said at least one heating element being located between the heat insulator and the first surface of the substrate, the layer of said at least one temperature measuring element being located facing the second surface of the substrate.

According to this arrangement, the layer of the heating element and the layer of the temperature measuring element are located on either side of the substrate.

This arrangement makes it possible to separate said at least one temperature measuring element from said at least one heating element.

For example, the substrate placed between these two operating layers is a heat conductor with a thickness that is less than or equal to 300 µm.

According to one characteristic, the thickness of the substrate is chosen such that the temperature measuring element is nearer the fluid than the heating element so that the wall temperature measured by the temperature measuring element is as representative as possible of the skin temperature and is not overly influenced by the heat flow generated by the heating element.

This arrangement is thus more sensitive and more reactive than the preceding arrangement.

The invention calls for using the sensor briefly described above to measure or detect the fouling that has formed (or is forming) on the sensor that is installed in one wall of a container (for example, industrial piping or an industrial reactor) containing a fluid.

More generally, the fouling forms on the outside surface of the sensor that is exposed to the fluid.

This outside surface corresponds either to the outside surface of said at least one interface element when the sensor is manufactured with such an element, or the outside surface of a separate interface material against which the sensor can be positioned.

Thus, the sensor measures the local wall temperature and determines the temperature deviation when a weak electrical output is applied to said at least one heating element.

Based on this temperature deviation, the thickness of the fouling that is forming naturally (i.e., not induced, for example, by heating said at least one interface element) on the outside surface of the sensor is determined continuously and in real time (no comparison with prerecorded reference measurements is necessary).

According to one characteristic, at least the outside surface of the sensor is representative of the state of the surface of one wall of the container that is in contact with the fluid, for example by the nature of the material and/or by its roughness.

Thus, by adapting this outside surface, depending on the environment in which the sensor is going to be placed, it is ensured that the latter will behave like an element that is part of this environment and not like a foreign body.

In particular, by reproducing, at least on the outside surface of the interface element or of the material, the state of the surface of the wall of the container with which the sensor is going to be associated, the formation of possible fouling on this outside surface will be very highly representative of the phenomenon of fouling on the wall of the container.

Thus, the surface state of the outside surface of the interface element or of the interface material depends on the state of the inside surface of the wall or walls of the container, state of the surface that depends on the anticipated applications.

According to one characteristic, the outside surface of the sensor has a roughness that is equivalent (for example identical) to that of a wall of the container that is in contact with the fluid.

This adaptation makes it possible to refine the similarity between the outside surface of the sensor and the wall of the container.

By way of example, the interface element or the interface material can be made of stainless steel, for example, of class 316L if the fluid is in a container made of stainless steel 316L or even of polyvinyl chloride (PVC) if the fluid is in a PVC container.

Generally, the interface element is made of the same material as that of the wall of the container to ensure that the surface state of the wall and the fouling phenomenon are representative.

A sensor or at least the interface element or the interface material of the sensor is thus dedicated to a given application, and at least a given situation.

However, if the interface element of the sensor or its outside surface is not representative of the state of the surface of the container walls, the sensor can nevertheless be used to detect the fouling in a relative manner (for example by detecting the increase and the decrease of the deposits).

Thus, the interface element or the outside surface of the sensor do not need to be similar to the container wall in this operating mode, in which the signal supplied by the sensor is used as an indicator.

In the case in which a separate interface material is used, the implementation of this additional interface material can be done separately from the sensor and matched to the intended application or applications. This additional interface material will be assembled on the sensor but ultimately at the manufacturing phase of this sensor. This approach allows the manufacture of a large number of microsensors according to their elementary structure, i.e., comprising the heating element or elements, the temperature measuring element or elements, and the heat insulator.

Moreover, the presence of the interface element in contact with the fluid, flowing or not, protects the sensor, at least mechanically, or equally chemically, and makes it resistant to external attack, especially originating from the fluid.

According to one characteristic, the sensor comprises at least one heat-conductive interface element with two opposite surfaces, one of the so-called inside surfaces being located against the temperature measuring element. The other so-called outside surface is designed to be in contact with the fluid.

Such an interface element protects the temperature measuring element as well as the rest of the sensor and is chosen (material and thickness) so as to offer as little heat resistance as possible.

According to one characteristic, said at least one interface element has (between its two opposite surfaces) a heat resistance that is less than or equal to $10°$ C./W.

This characteristic of the interface element makes it possible to ensure that the heat flow that is generated will be effectively diffused as far as the outside surface and will be evacuated by the fluid without encountering strong heat resistance that would risk causing a temperature increase that is harmful to proper operation of the sensor. Moreover, this makes the sensor more sensitive, more reactive and more reliable.

It should be noted that the thickness of the material of the interface is thus adapted depending on the material itself, taking into account the heat resistance that is not to be exceeded.

The object of the invention is a system for measuring or detecting a fouling that has formed directly or indirectly on a front surface of a sensor that is exposed to a fluid, the sensor comprising the following in the form of superimposed layers:
  At least one heating element that is able to diffuse, on command, a homogenous, monitored heat flow,
  A heat insulator located on the side opposite the front surface of the sensor for preventing dissipation of the heat flow from said opposite side,
  At least one temperature measuring element that is placed in the homogenous heat flow diffused by said at least one heating element,
  A substrate on which the layers of said at least one heating element and at least one temperature measuring element are connected, the system comprising:
  Means for determining a temperature deviation between, on the one hand, the wall temperature measured by said at least one temperature measuring element when said at least one heating element diffuses a heat flow, and on the other hand, the temperature of the fluid,
  Means for calculating the thickness of the fouling formed on the front surface of the sensor exposed to the fluid based on the determined temperature deviation.

According to one characteristic, said at least one heating element generates a heat output of less than 200 mW, and said at least one temperature measuring element offers measurement precision of better than $0.1°$ C.

The object of the invention is likewise a method for measuring and/or detecting the fouling that has formed on the front surface of a sensor that is exposed to a fluid when it has been installed in a wall of a container that contains the fluid, the sensor comprising the following in the form of the superimposed layers:
  At least one heating element that is able to diffuse, on command, a monitored homogeneous heat flow,
  A heat insulator located on the side opposite the front surface of the sensor for preventing dissipation of the heat flow from said opposite side,
  At least one temperature measuring element that is placed in the homogenous heat flow diffused by said at least one heating element,
  A substrate on which the layers of said at least one heating element and at least one temperature measuring element are connected.

The object of the invention is also a method that comprises the following stages:
  Determination of a temperature deviation between, on the one hand, the wall temperature measured by said at least one temperature measuring element when said at least one heating element diffuses a heat flow, and, on the other hand, the fluid temperature,
  Calculation of the thickness of the fouling formed on the front surface of the sensor exposed to the fluid based on the determined temperature deviation.

More particularly, the object of the invention is a process in which the determination of a temperature deviation comprises the following stages:
  Alternation of the phases for control of the diffusion of a heat output by said at least one heating element and for the absence of diffusion of a heat output, Permanent measurement of the wall temperature by said at least one temperature measuring element during each of the aforementioned phases, Determination of a temperature deviation between the temperatures measured by said at least temperature measuring element.

Thus, the measurement or detection of fouling is done by determining the temperature deviation provided by the wall temperature measuring element when said at least one heating element generates a heat flow and when it does not.

It should be noted that when a heat flow is not generated, the sensor that is especially sensitive and reactive measures the fluid temperature.

By way of example, in the absence of fouling on the outside surface exposed to the fluid, the temperature deviation is less than 0.1° C., while it can reach 2 to 3° C. in the presence of serious fouling.

According to one characteristic, the stage for control of diffusion of a heat flow by said at least one heating element comprises a stage for generation of an output modulation signal from said at least one heating element.

According to one characteristic, the signal is alternating and, for example, is steady-state.

According to one more particular characteristic, the steady-state alternating signal is in square waves.

According to one characteristic, said at least one temperature measuring element offers a temperature measurement precision that is better than or equal to 1% of the maximum temperature deviation determined between the unfouled state and the fouled state of the sensor.

Thus, for example, if a heat output of 10 mW is generated by the heating element and a maximum temperature deviation of 1 to 2° C. can be detected, then the measurement precision of said at least one temperature measuring element is roughly 0.01 to 0.02° C.

It should be noted that according to the invention, the use of a temperature measuring element or several temperature measuring elements of very high precision allows the use of one or more heating elements generating a very weak heat output, whereas temperature measuring elements of low precision would not allow the use of such a low heat output.

BRIEF DESCRIPTION OF THE DRAWINGS

Other characteristics and advantages will become apparent during the following description, given solely by way of nonlimiting example with reference to the attached drawings, in which:

FIGS. 2a to 2c and 2g to 2i schematically illustrate the stages of manufacture of the sensor according to the second embodiment;

DETAILED DESCRIPTION OF THE INVENTION

The purpose of this invention is to propose, especially based on the collective manufacturing processes of microelectronics in general, and based on processes for manufacture of microsystem technologies in particular, a sensor of small dimensions able to determine fouling in a fluid that is flowing or at rest.

It should be noted that a miniaturized sensor according to the invention can be alternatively manufactured according to techniques other than serigraphy.

Figure 1A:
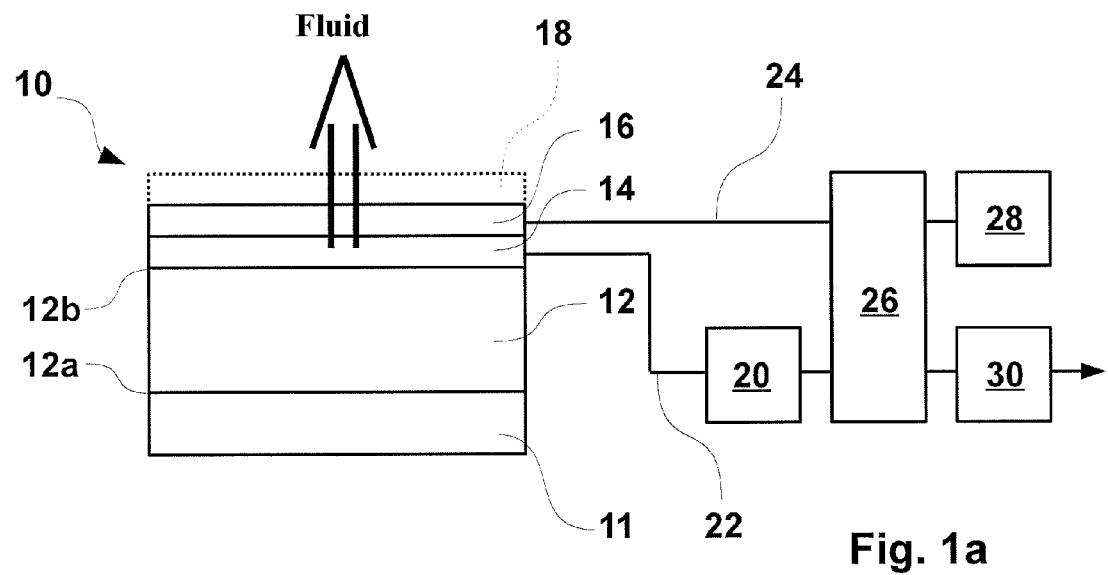
FIG. 1a is a general schematic view of a sensor according to a first embodiment of the invention and associated means allowing its implementation.

As shown schematically in FIG. 1a, a sensor 10 produced by using microsystem manufacturing technologies according to a first embodiment of the invention comprises several operating elements assembled with one another on a substrate 12 with two opposite surfaces 12a, 12b, i.e.:

At least one heating element 14 made in the form of a layer that is deposited on the surface 12b of the substrate 12 and that diffuses, on command, a monitored homogenous heat flow, At least one temperature measuring element 16 that is made in the form of a layer that is deposited on the layer 14 and that is located in such a way as to be in the most homogeneous part of the dissipated heat flow (when there is only one element 16 and it is at the center of the active zone of the heating element or elements), A heat insulator 11 in contact with the surface 12a of the substrate (the insulator is, for example, a Teflon block that is 400 µm thick with 0.25 W/mK of heat conductivity), And, optionally, at least one heat-conductive interface element 18 that is made in the form of a layer deposited on the layer 16 and that protects the sensor from external attack.

In this example, the sensor is thus made in the form of a plurality of superimposed heterogenous layers.

The temperature measuring element 16 is, for example, in a surface ratio with the heating element 14 (more exactly with the active zone of the heating element), less than 2%, i.e., the size of the element 16 is at least 50 times smaller than that of the element 14.

FIG. 1a does not show the operating elements within the layers for reasons of scale and readability.

The temperature measuring element is characterized by high measurement precision of better than 0.1° C., more especially between 0.005 and 0.01° C., which allows it to work with one or more heating elements generating a weak heat output.

The generated heat output is between 1 and 50 mW. This output is, on the one hand, sufficient for the measuring element 16 to be able to very sensitively measure a temperature, and, on the other hand, weak enough to not influence the measurement medium (fluid).

Actually, it is necessary to avoid heating the medium in order to avoid, for example, inducing unnatural fouling on the sensor.

The low output value and the high measurement precision allow the sensor to be very sensitive, very reactive and very reliable in the measurement and/or the detection of fouling, without, however, being perturbed by the measurement conditions in general and by the fluid circulation in particular.

The layer of said at least one heating element 14 that is supplied by the electric power supply means 20 (example: current or voltage generator able to provide an electrical output on command) via connection means 22, diffuses a homogeneous and monitored heat flow illustrated by the vertical arrow on the figure.

This flow is dissipated toward the front surface of the sensor (surface that is intended to be in direct or indirect contact with the fluid and that is either the free surface of the layer 18 or the free surface of the layer 16) opposite the back surface of the sensor where the heat insulator is located due to the presence of this insulator.

More generally, the dissipation of the flow is prevented on the rear surface of the sensor by the heat insulator.

The layer of said at least one temperature measuring element 16, placed in this homogeneous and known heat flow, measures the wall temperature continuously or intermittently and transmits these measurements via the connection means 24 to a data processing unit 26 or computer (including, for example, a microprocessor and memories).

When the layer of said at least one interface element 18 is present, it transmits the heat flow toward the outside of the sensor, in the direction of the fluid medium in which it is placed, and dissipates this heat.

The data (for example wall temperature measured by the element 16 and output induced in the element 14) are collected by the unit 26.

This unit 26 samples and converts into physical quantities (temperature, . . . ) the measurements and data originating from the sensor as well as the generated output. It should be noted that the system for determination of fouling that is formed by the sensor and in particular elements 20 and 26 comprises means (unit 26) for determining a temperature deviation between the temperatures measured by the measuring element and means for calculating (unit 26) the thickness of the fouling formed on the surface of the sensor based on this temperature deviation that has been determined in this way and physical formulas of the geometry of the known sensor.

More particularly, the means of determination measure a temperature deviation between, on the one hand, the wall temperature measured by the temperature measuring element when the heating element dissipates a heat flow, and, on the other hand, the fluid temperature. Moreover, the system optionally comprises a display 28 and/or means 30 for remote data transmission. The display 28, for example, allows continuous display of the values of temperature (measured) and fouling (calculated), as will be seen below, for example in the form of curves representing the time progression of the temperature and/or of the fouling thickness. The means 28 (example: transmitter) allow remote sending of data measured and/or processed by the unit 26 and/or alarm information and/or other information relative to the sensor and/or to its operating state.

Figure 1B:
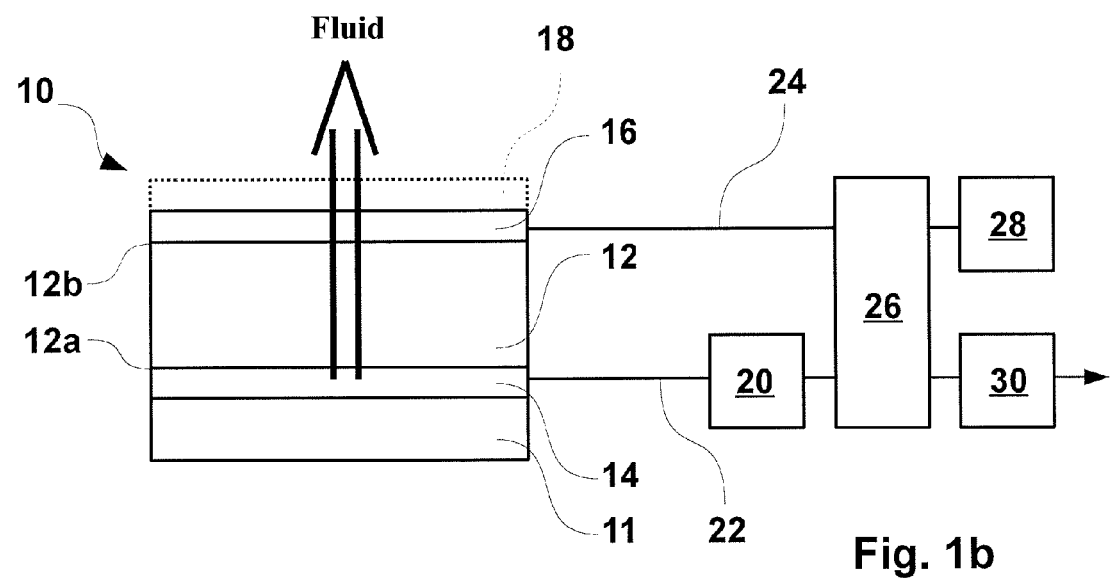
FIG. 1b is a general schematic view of a sensor according to a second embodiment.

FIG. 1b illustrates a sensor 10 made by using, for example, microsystem manufacturing technologies according to a second embodiment of the invention.

The operating elements already described in relation to the sensor illustrated in FIG. 1a remain the same and are therefore not described again.

The arrangement of the sensor of FIG. 1b is different from that of FIG. 1a to the degree in which the heating element 14 and the temperature measuring element 16 are located, not on the same side of the substrate 12, but on either side of the latter.

Actually, the temperature measuring element 16 is located facing the surface 12b of the substrate and, for example, in contact with the latter (while one or several intermediate layers can be located between these two elements), and the heating element 14 is located between the surface 12a of the substrate and the heat insulator 11.

In this arrangement, the two operating elements 14 and 16 of the sensor are spaced apart from one another at a distance corresponding essentially to the thickness of the substrate 12.

This thickness can be on the order of several hundred microns and, for example, 300 microns.

This arrangement makes it possible to reduce the direct influence of the heating element on the temperature measuring element in order to improve sensor performance.

Due to this arrangement, the temperature measuring element or elements 16 will measure a wall temperature that is nearer that of the fluid than that of the heating element.

The measurement of fouling that results therefrom will therefore be more reliable.

Moreover, the sensor is thus more sensitive.

It should, however, be noted that the temperature measuring element is always in the homogeneous part of the heat flow generated by the heating element in spite of this deviation between the two elements.

It should be noted that for certain functionalities of the sensor, it can be envisioned that certain micromachining operations be provided on one or more aforementioned layers.

The description of a microsystem sensor and a process for manufacturing the latter will now be carried out with reference to FIGS. 2a-i and 3 to 7.

FIGS. 2a to 2f illustrate a process for manufacturing the sensor of FIG. 1a, whereas FIGS. 2a to 2c and 2g to 2i illustrate a process for manufacturing the sensor of FIG. 1b.

The stages 2a to 2c are common to the two processes and will now be described.

Figure 2A:
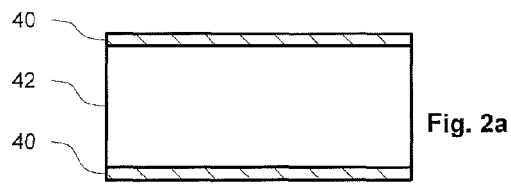
FIGS. 2a to 2f schematically illustrate the stages of manufacture of the sensor according to the first embodiment.

In FIG. 2a, an electrically insulating layer 40 is first deposited on a receiving substrate 42, for example made of silicon, of a given thickness (for example 300 μm). A passivation layer 40 can be formed on the two opposite surfaces of the substrate (FIG. 2a). This insulating layer 40 can be a silicon oxide monolayer deposited thermally or a silicon nitride monolayer of a thickness in the μm range. It can be alternately composed of a bilayer that is generally composed of a first silicon oxide layer on which a second silicon nitride layer is deposited. The thicknesses that are commonly used are 0.7 μm for $SiO_2$ and 0.8 μm for silicon nitride.

Figure 2B:
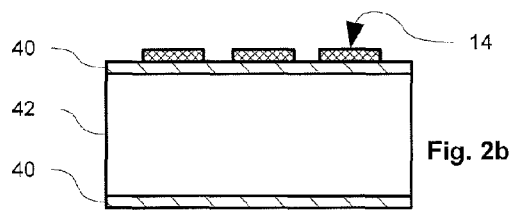

As shown in FIG. 2b, a layer 14 composed of one or more heating elements (a single heating element is shown in this embodiment) is formed by a metallic deposition on one of the insulating layers 40 (for example, the upper layer).

The heating element 14 is configured in such a way as to optimize and enhance the formation of a heat flow. The metal is deposited in the form of one or more resistive tracks or lines of small width forming a more or less complex geometrical figure according to the desired physical characteristics (here, the heat flow to be produced by the heating element) by covering one or more zones, i.e., more or less the entirety of the layer 40. These lines appear on the resistive metallic tracks formed by, for example, serigraphy on a printed circuit substrate. These lines are designed in such a way as to form one or more meanders 40a (FIG. 3) or else concentric lines 40b (FIG. 4). The heating element is composed either of a monolayer of a platinum (Pt)-type metal or else a bilayer of the titanium/platinum (Ti/Pt) type. The first titanium layer is a coupling layer that allows the platinum layer to increase its adhesion. It is likewise designed to increase, during a heating phase, its mechanical resistance that is engendered by the variation of stress in this layer. The objective is to limit to the maximum degree the effects of detachment and by the same token increase the service life of the heating element. This heating element can likewise be made of doped silicon.

Figure 3:
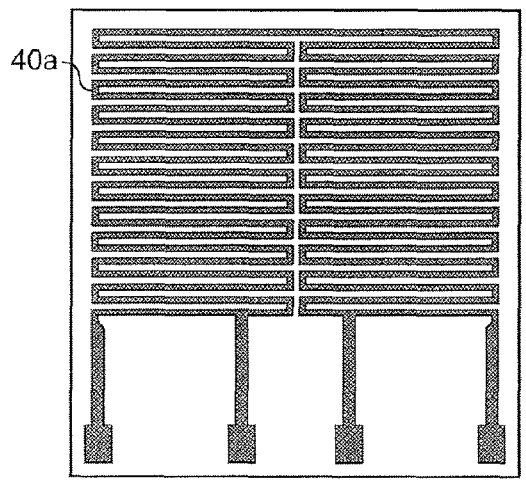
FIGS. 3 and 4 schematically illustrate two embodiments of the layer of the heating element respectively.
Figure 4:
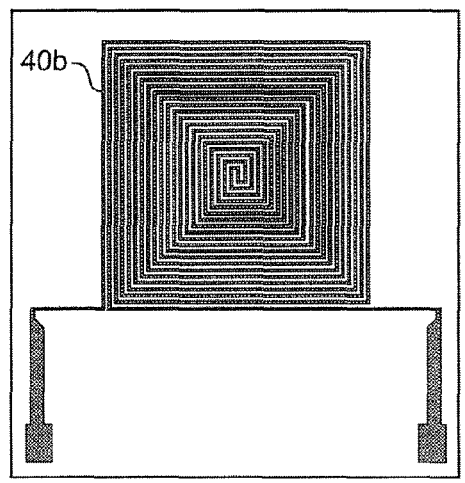

It should be noted that the heating element of FIGS. 3 and 4 comprises connection tracks or contacts that allow the necessary electrical power, originating from the device 20, to be provided to this element.

In particular, the heating element of FIG. 3 comprises four electrical connection contacts that are used for, for example, test or measurement purposes by implementing the known four-point technique.

The dimensioning of the heating element or elements is done with the following formula:

$$R_{heat} = \rho \cdot (L/s)$$

where $\rho$ is the resistivity of the material constituting the heating element, L is the length of the wire comprising the heating element, S is the surface of the heating element defined by the following formula, $$S = h * l$$

where l is the width of the heating element and h is its height.

The dimensioning of the heating element is done by determining the heat flow necessary to be able to detect fouling on the sensor surface depending on the intended application.

The injection of electrical current or voltage into the heat resistor generates overheating of the latter. A heat flow is then generated and varies depending on the output injected into the heating element. The value of its resistance at rest is calculated depending on the output of the heat flow to be generated.

By using microsystem technologies (small sizes of the elements), the output injected into the heating element is very weak, for example roughly 10 mW (this corresponds to a current of intensity of between 0.1 and 10 mA); this is especially advantageous.

It should be noted that the heating element is thus made, for example, in the form of platinum resistive tracks that are 40 μm wide and 2 μm thick and whose electrical resistance is 3.2 kΩ at 20° C.

The size of the active surface of the heating element is, for example, 25 mm² (corresponding to a square of 5 mm per side).

The heat output generated by such an element is between 5 and 50 mW, and more especially between 5 and 10 mW. For its part, the output density is between 0.2 and 2 mW/mm².

Figure 2C:
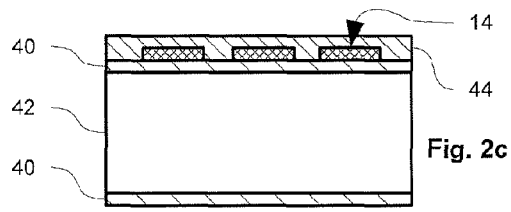

An electrically insulating layer 44 is deposited on the layer of the heating element 14 (FIG. 2c). This dielectric layer, for example of silicon nitride, is deposited according to the known deposition technique under the name PECVD. The first role of this layer is to eliminate any risk of short circuit between the heating element 14 and the next layer to be deposited (measuring element) during operation that will be described below. The second role of this layer is to level the topography caused by the presence of the heating element in order to facilitate the deposition of the measuring element.

The stages 2d and 2f of the process for manufacturing the sensor of FIG. 1a will now be described.

A layer 16 comprising one or more temperature measuring elements is deposited on the insulating layer 44 described above (FIG. 2d). This layer is configured in such a way as to optimize the variation of its resistive characteristics depending on the temperature. The distribution of a heat flow during a heating phase of a heating element is homogeneous to the center of the latter and becomes intermittent when moving away from its center. Consequently, the temperature measuring element is deposited above the heating element 14, made, for example, according to the configuration 40b of FIG. 4, on the dielectric layer 44. The measuring element 16 is located centered on the heating element, and its size is much smaller than that of said heating element in order to be placed in the most homogeneous part of the flow at the heart of that of the heat flow, thus avoiding the perturbations caused by the edge effects.

Figure 5A:
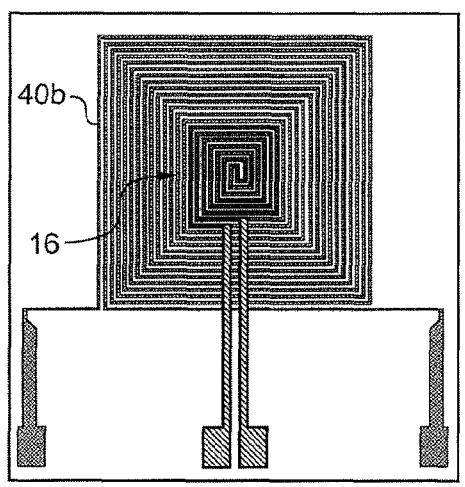
FIG. 5a schematically illustrates the superposition of one layer of a temperature measuring element and of the layer of the heating element of FIG. 4.

FIG. 5a shows the centered and superimposed position of one temperature measuring element 16 above one heating element.

Figure 5B:
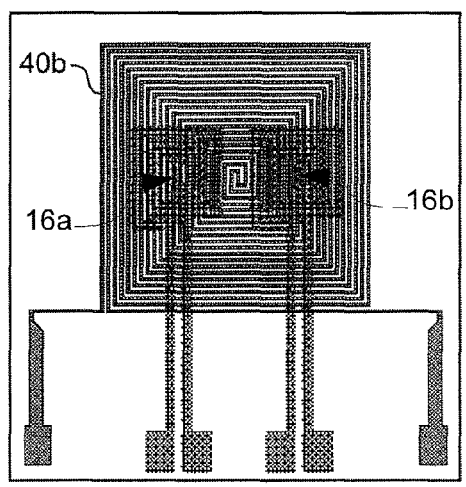
FIG. 5b illustrates the superposition of a layer comprising two temperature measuring elements and the layer of the heating element of FIG. 4.

It should be noted that several temperature measuring elements can be placed in the heat flow and distributed at a distance from one another as shown in FIG. 5b. In this figure, two measuring elements 16a and 16b are arranged in the central part of the heating element to be at the heart of the homogeneous and known flow, but they are separated from one another to be able to determine the fouling at two distinct sites of the sensor surface. More than two elements can be used according to needs and applications.

The geometry adopted to build this measuring element is known to one skilled in the art. One or more resistive metallic lines arranged in the form of meanders (FIG. 6) or else concentric lines (FIG. 7) can be used in the same way as described above for the heating element with reference to FIGS. 3 and 4. The temperature measuring element or elements are composed either of a metal monolayer, for example made of platinum, or a bilayer of type Ti/Pt. The first titanium layer comprises the attachment layer.

The temperature measuring element 16 is thus, for example, implemented in the form of platinum resistive tracks that are 20 μm in width and 2 μm in thickness and whose electrical resistance is 3 kΩ at 20° C. The measurement precision is, for example, 0.005° C. with adapted electronics (having, for example, a precision of 20 bits).

The size of the surface of the temperature measuring element is, for example, 0.49 mm² (which corresponds to a square of 700 μm per side).

It should be noted that the measuring element of FIGS. 5a and 5b, 6 and 7 comprises connecting tracks or contacts that allow the necessary electric energy to be supplied to this element, originating from the device 20, and to collect temperature data at the level of the unit 26.

Figure 7:
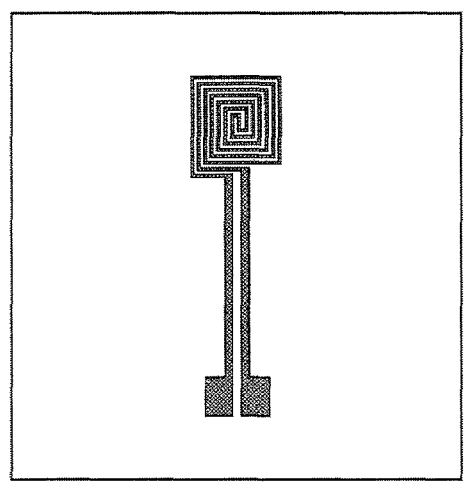

The measuring element such as that of FIG. 7 can be implemented by using, for example, the well-known technique of two points that allows, knowing the voltage and electrical intensity, direct deduction of the resistance value from it.

This measurement is used when the measurement noise or the noise associated with the measurement is not too high, and it is this that is used in the assembly of FIGS. 5a and 5b.

Figure 6:
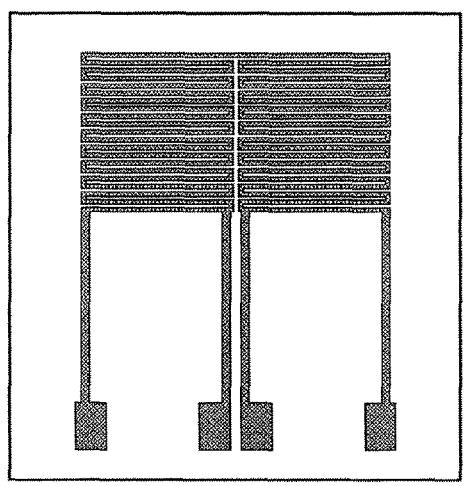
FIGS. 6 and 7 schematically illustrate two embodiments of the layer of the temperature measuring element respectively.

When the noise is too high, the measuring element such as that of FIG. 6 can be implemented by using, for example, the well-known technique of four points. According to this indirect measurement technique, the value of the voltage applied to the terminals is known, the value of the intensity is measured, and the resistance value is deduced from it.

It should be noted that the four points technique can likewise be used for test purposes.

Figure 2D:
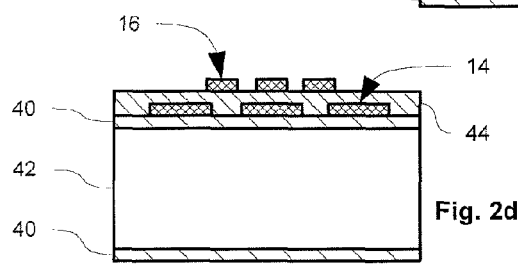
Figure 2G:
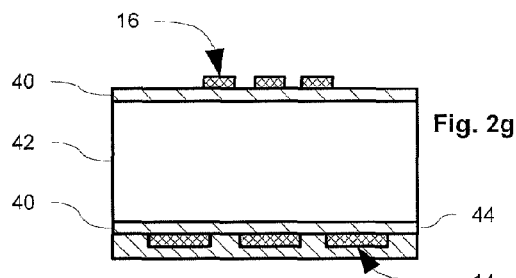
Figure 2E:
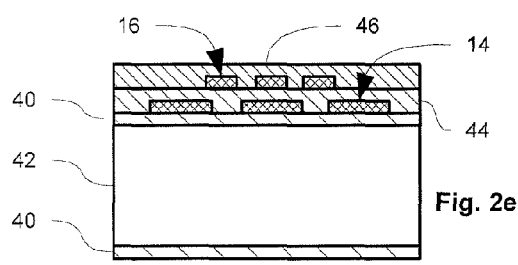

An insulating layer 46 is deposited on the layer of the temperature measuring element (FIG. 2e). This electrically insulating layer is deposited on the measuring element. The first role of this layer is to eliminate any risk of short circuit between the measuring element and the next layer to be deposited (interface element(s)) during the operation that will be described below.

The second role of this layer is to level the topography of the microsystem during manufacture. Deposition of a dielectric layer according to the known technique called PECVD makes it possible to limit the overly large profile variations.

The thickness of this layer as explained above must be sufficient, on the one hand, to eliminate any risk of short circuit between the measuring element and the interface layer when it is present, and, on the other hand, to consequently reduce the reliefs produced by the topography caused by the presence of the measuring element and thus to offer a surface that is as flat as possible.

Optionally, a protective layer 18 formed from at least one interface element is deposited on the insulating layer 46 (FIG. 20 by techniques that are well known to one skilled in the art (ex.: PEVCD). This layer can be composed of, for example, a metal layer or a dielectric layer.

As already mentioned, the process for manufacturing the sensor of FIG. 1b comprises the stages 2a to 2c that have already been described and the stages 2g to 2i that will now be briefly described.

FIG. 2g corresponds to the stage of application or deposition of a layer 16 comprising one or more temperature measuring elements on the insulating layer 40 located under the substrate 42 of FIG. 2c.

Figure 2H:
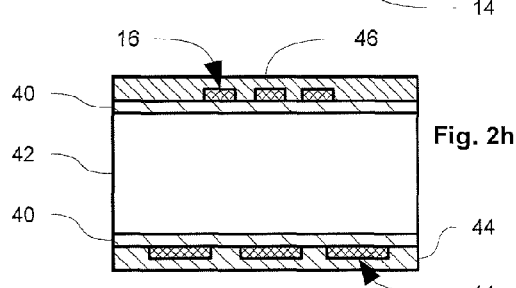
Figure 2F:
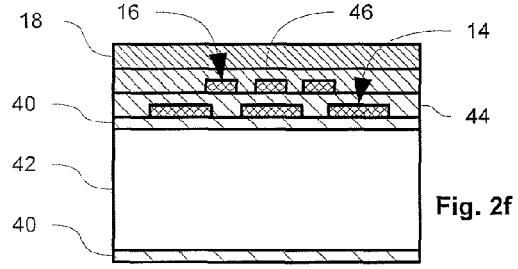

In FIG. 2g, the arrangement of FIG. 2f has been reversed, and the heating element 14 is in the bottom part, under the substrate 42.

The stage consisting in depositing the temperature measuring element or elements 16 is identical to that which was described with respect to FIG. 2d if it is only that the temperature measuring element or elements are thus located on the side of the substrate that is opposite the side on which the heating element 14 is located.

The stage illustrated in FIG. 2h corresponds to the application or the deposition of an insulating layer 46 that is identical to that described in relation to FIG. 2e described above.

In the same way as for FIG. 2f, an optional protective layer 18 playing the part of an interface element is deposited on the insulating layer 46 above the temperature measuring element or elements 16.

Figure 2I:
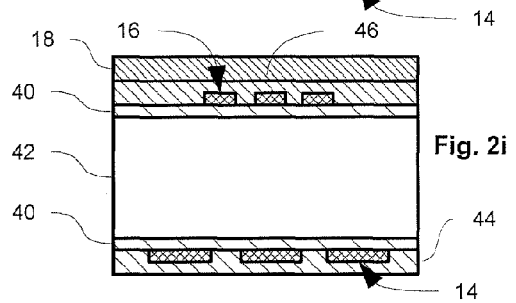

The characteristics and advantages described in relation to the stages of the part of the manufacturing process illustrated in FIGS. 2d to 2f remain valid for FIGS. 2g to 2i and therefore will not be repeated.

Figure 8:
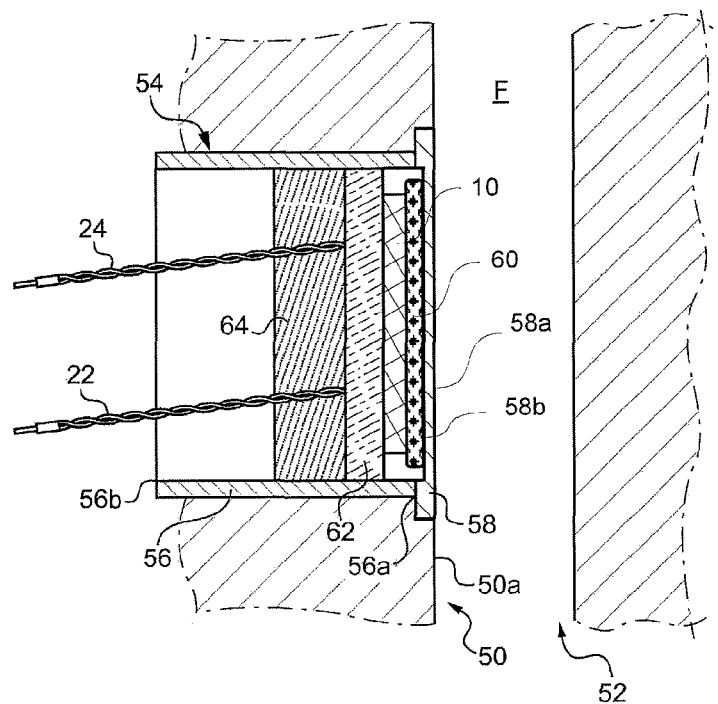
FIG. 8 is a schematic view showing the implantation of a sensor according to the invention in a body mounted on one wall of a container.

FIG. 8 illustrates one embodiment in which the microsystem sensor 10 according to the invention is linked to one wall 50 of a container 52 (for example a chemical reactor or even a vat) in which a fluid, here stagnant, marked F, is present.

It should be noted that the container 52 that contains the fluid can be of a type other than a line or a piping of an industrial installation, . . . .

It should also be noted that the fluid present in the container is not necessarily at rest but can be flowing.

The microsystem sensor 10, such as is shown schematically in FIG. 1a or 1b, is mounted on one of the walls of the container as indicated on FIG. 8 via a body 54 in which the microsystem 10 is integrated.

More particularly, the sensor 10 is arranged in a hollow cylindrical jacket 56 provided on one of its longitudinal ends 56a with a plate 58 that forms a shoulder and that has, for example, the shape of a disk or tablet. This plate is, for example, welded to the cylindrical jacket 56.

It should be noted that other shapes of the body can be envisioned without adversely affecting the operation of the sensor.

The plate 58 that forms the shoulder is designed to be inserted into an arrangement provided accordingly in the wall 50 of the container in order to be mounted flush relative to the latter.

The plate 58 that forms the shoulder can likewise be assembled on a cylinder that is to be inserted into the wall 50 of the container having a hole (or point of attack) that already exists and that is provided for this purpose.

This plate 58 is narrowed in its central part where the sensor is positioned, and comprises a material or interface element that is in contact with the fluid F by its outside surface 58a.

It should be noted that the surface 58a and the surface 50a can be arranged on the same side in order not to introduce perturbation into the flow.

In this embodiment, the interface element 18 of the sensor of FIGS. 1a and 1b is not present, the plate 58 playing the part of interface element.

To maximize the heat exchange between the heating element of the microsystem sensor 10 and the inside surface 58b of the plate 58, a heat transmission element 60 such as a thermal paste with a high coefficient of heat conductivity can be used and placed in contact with the microsystem. More particularly, this element 60 is located on the active zone of the microsystem composed of more or less the entirety of its outside surface except maybe a small peripheral zone (the sensitive elements of the microsystem being instead arranged centered). This assembly is then arranged against the rear or inside surface 58b of the interface material 58.

Moreover, as shown in FIG. 8, the microsystem sensor 10 is mounted on a substrate 62 such as a printed circuit board whose role is to form the electrical contacts that are necessary between this microsystem sensor and the part of the associated system that ensures electrical supply and processing of the information from this sensor. These electrical contacts work with the tracks or contacts illustrated in FIGS. 3 to 7 and briefly described above. This part of the measurement system has been shown in FIGS. 1a and 1b by the elements 20, 26, 28 and 30 that are connected to the sensor via the connections 22 and 24.

In order to maximally concentrate the monitored and homogeneous heat flow generated by the heating element toward the front of the microsystem sensor 10, i.e., toward the measuring element and the interface material, an additional heat insulating element 64 is introduced into the body 54 by the back end 56b. This element 64, such as a paste with a low coefficient of heat conductivity, is arranged against the back surface of the support 62 in order to form an additional thermal shield to the rear of the body and thus to promote dissipation of the heat flow toward the front of said body.

It should, however, be noted that the heat insulator 11 of FIGS. 1a and 1b already ensures a satisfactory barrier function to the heat flow on the back surface of the sensor.

Moreover, additional heat insulation that is not shown is likewise implemented between the plate 58 and the cylindrical jacket 56 of the body 54. The role of this heat insulator, which can consist of a heat insulating paste or else a ceramic washer that is not shown, is to eliminate any risk of a heat bridge between the interface material 58 and the jacket 56 during a heating phase.

The plate 58 playing the part of the interface material with the fluid is adapted at least so that its outside surface 58a is representative of the state of the surface of the wall 50 of the container so that the deposition of a fouling layer on the surface 58a is done more or less identically to the deposition of a fouling layer on the inside surface 50a of the wall of the container.

Actually, it is on the outside surface 58a of this plate that the fouling phenomenon will be revealed according to the invention, having understood that this phenomenon is, of course, produced at other locations of the inside surface 50a of the wall.

Thus, the determination of the fouling formed on the surface 58a, a determination that corresponds either to a measurement of fouling or to a detection of fouling, will be particularly reliable, considering the nature of this outside surface and likewise considering the microsensor that is especially sensitive and generates very few perturbations capable of altering the fouling phenomenon.

In order that the outside surface 58a be representative of the state of the surface of the wall of the container, it is preferred that this surface have a roughness equivalent—namely identical—to that of the wall.

Thus, for example, within the framework of an agricultural application, the wall 50 can be made of stainless steel, for example stainless steel of class 316L, and the surface 58a of the sensor can be made in such a way as to have a surface roughness of less than or equal to 0.8 μm, just like that of the surface 50a of the wall.

Preferably, the outside surface 58a is made of a material of the same type as that of the wall of the container. If this material is not identical, it must be at least of a nature compatible with that of the material constituting the wall.

The simplest approach is that the interface element 58 is made of a material that is identical to that of the container wall.

In this example, the plate 58 just like the cylindrical jacket 56 are made of stainless steel, a material that is the one used for the wall 50 and especially its inside surface 50a.

The plate 58 is a heat conductor that has a heat resistance that is less than or equal to 10° C./W in order to impart good sensitivity and a high signal-to-noise ratio to the sensor.

The material used and its thickness are thus chosen to offer very low heat resistance to the heat flow. The thickness is, for example, 300 μm.

It should be noted that the sensor according to the invention can only comprise a single temperature measuring element.

The temperature of the fluid and, more generally, of the industrial process that dictates the container is generally not known.

For all that, this has no effect on the process of measurement and/or detection of fouling formed within the container, as will be seen below.

The process makes it possible to avoid possible variations of this temperature over time.

It should be noted, however, that the microsystem sensor according to the invention can comprise more than one temperature measuring element according to the anticipated applications. Likewise, it can equally comprise several heating elements in interaction with a single temperature measuring element or even with several of these elements.

Figure 9:
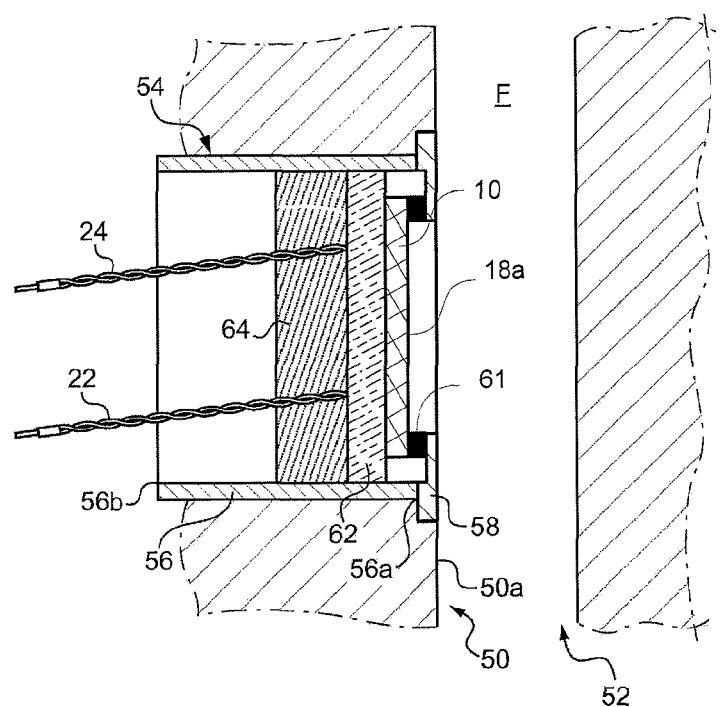
FIG. 9 is a schematic view showing the implantation of a sensor according to the invention in one wall of a container.

FIG. 9 schematically illustrates the direct installation of a microsystem sensor such as the one of FIGS. 1a, 1b, 2f and 2i in a wall 50 of a container 52.

In this embodiment, the sensor 10 is in direct contact with the fluid F by the outside surface 18a of its interface element 18 instead of using the interface material 58 of FIG. 8.

The sensitivity of the thus arranged sensor is therefore increased, by itself providing better results than in the case of FIG. 8.

It should be noted that the sensor 10 is not actually mounted flush relative to the wall, but is very slightly set back relative to the latter. This set-back has been intentionally exaggerated to illustrate it in the figures. In practice, it is, for example, a few hundred microns, for example 500 μm.

The elements of FIG. 9 that are unchanged relative to FIG. 8 keep the same references and will not be described again.

A seal 61 is provided on the periphery of the outside surface of the sensor to ensure the mounting seal.

Moreover, all of the characteristics and advantages described above with reference to FIG. 8, especially regarding the interface element 58 surface (state of the outside surface 58a, conductive properties), apply here to the interface element 18a of the sensor.

The measurement process will now be described with reference to FIGS. 10 and 11 according to a first embodiment of the invention that applies equally well to the configuration of FIG. 8 and to that of FIG. 9.

This process allows measurement and/or detection of the fouling that forms on the outside surface 58a of the interface material 58 of FIG. 8 or on the outside surface 18a of the interface element 18 of FIG. 9.

"Fouling" is defined as any adhering deposit that forms on the surface of the element under consideration from bodies that are temporarily or permanently in the fluid (fouling of an organic nature, such as a biofilm, or of an inorganic nature, such as scaling).

It should be noted that the process according to the invention allows measurement and/or detection of fouling on site, in line and continuously, and more or less in real time.

It is therefore not necessary to take samples on site and later to analyze the samples taken for purposes of measurement and/or detection of fouling.

The process according to a first embodiment calls for alternating the phases for control of diffusion of a heat flow by the heating element or elements 14 of the sensor and for the absence of diffusion of a heat flow over a given time interval.

Moreover, the process during this interval calls for continuous measurement of the surface temperature of the interface element in contact with the measurement medium by the element for measuring the temperature (or only the local temperature of the site where the temperature measuring element is positioned in the absence of the interface element).

For example, this alternation of phases of heating and no heating of the sensor is possible throughout the progression of an industrial process or only during certain stages of the latter.

The operation of measuring the fouling makes it possible to know, at any time, the thickness of the layer of fouling that has formed on the surface of the interface material or directly of the sensor and that very reliably reproduces the fouling that has formed on the inside surface of the container in which the sensor is installed.

Moreover, when the sensor is used to perform a detection function, it can be used to trigger an alarm signal in case of detection of a layer of fouling in the course of formation or exceeding a predetermined threshold.

As already disclosed above, the device 20 generates an electrical output that is transmitted to the heating element, for example in the form of an output modulation signal that is, for example, of the alternating type.

This signal is preferably steady-state, i.e., it defines perfectly determined stable states during which either a determined electrical output is supplied to the heating element, or no output is supplied to this element.

Figure 10:
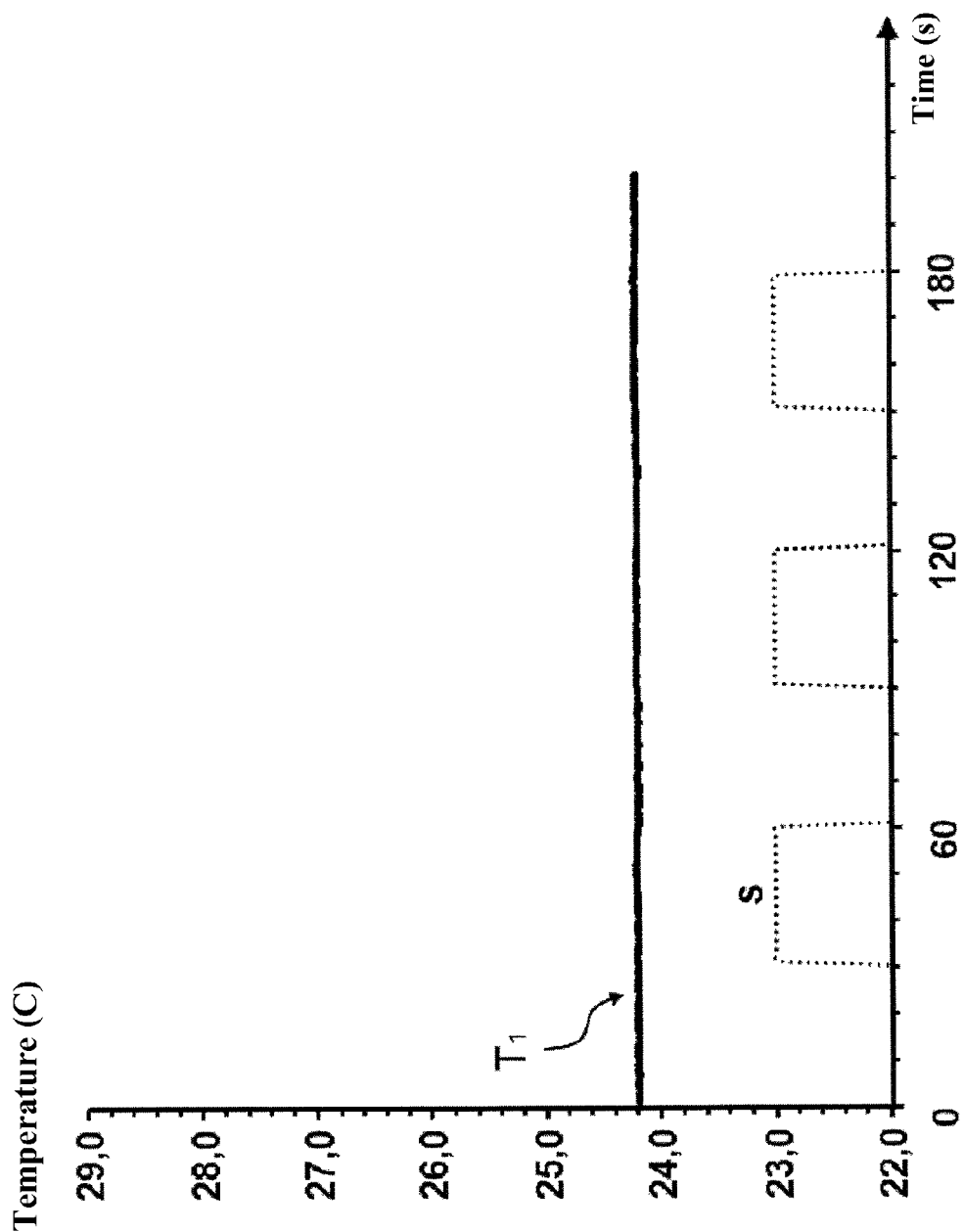
FIGS. 10 and 11 illustrate the temperature measurements taken by a sensor according to the invention, in the presence and absence of fouling relative to a supply signal S, respectively.

FIG. 10 illustrates an alternating steady-state signal produced in the form of square waves.

More especially, FIG. 10 illustrates, on the one hand, in the lower part, the output signal in the form of square waves S that is applied to the heating element and, on the other hand, in the upper part, the temperature measured by the measuring element during each of the phases of heating and no heating.

The different measurements of temperatures show that the latter remain essentially constant (around a value $T_1$); this expresses an unfouled state of the sensor and therefore of the inside wall of the container.

The temperature T1 corresponds to the temperature of the fluid.

When the surface state is clean, the heat flow produced by the heating element is transferred to the measuring element and to the interface element, and is then diffused into the measurement medium, and the temperature measured by the measuring element remains essentially constant and equal to the temperature of the medium.

Conventionally, when fouling is forming on the outside surface of the sensor and therefore on the inside surface of the wall of the container, the heat flow generated by the heating element will cause an increase of the temperature at the level of the interface element or of the interface material. Actually, in the course of formation, the fouling layer acts as a heat insulator (heat barrier) that thus reduces heat exchanges with the measurement medium and therefore the dissipation of the flow.

The temperature deviation that appears will be taken into account, as will be seen below, for determining the value of the thickness of the fouling.

Figure 11:
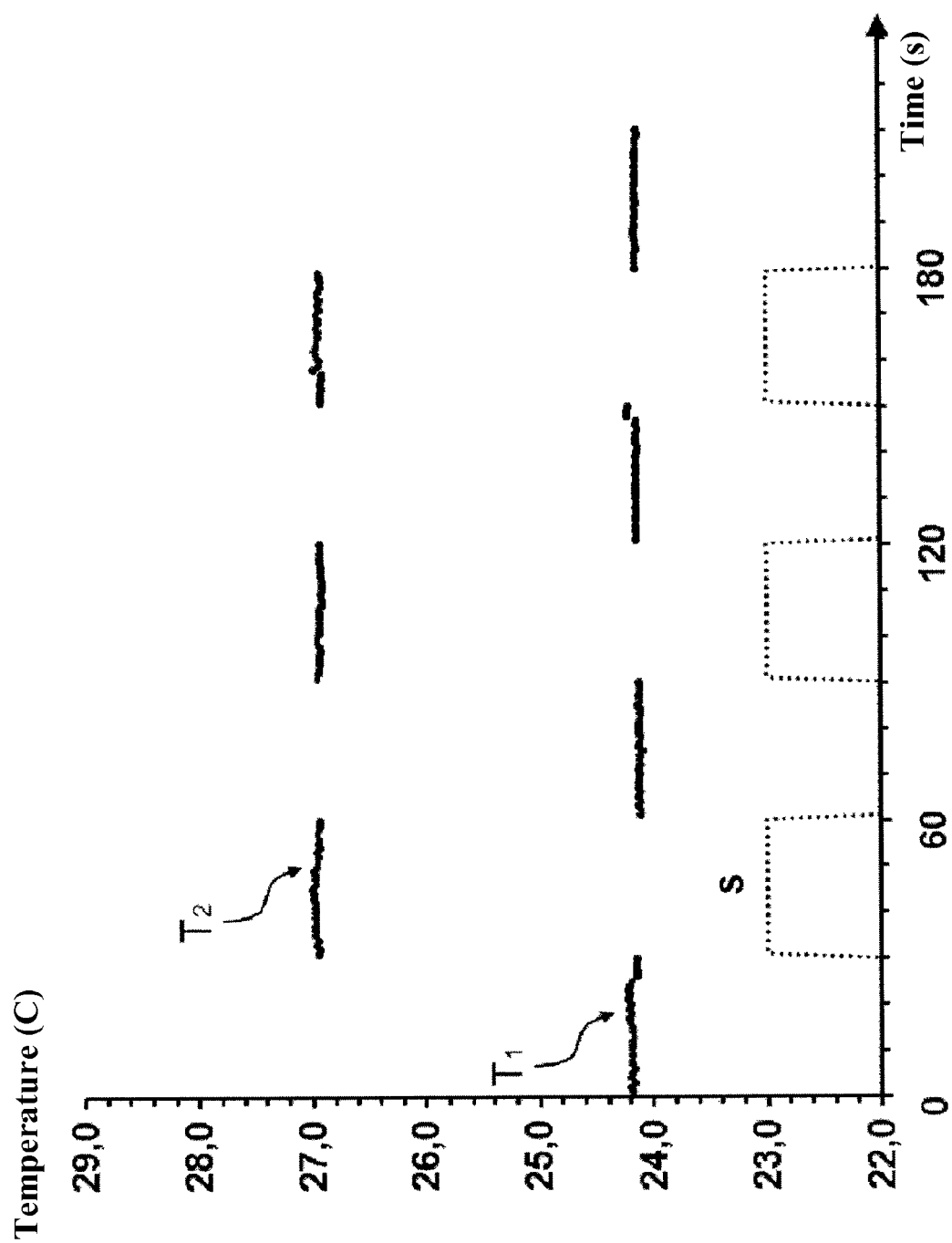

This phenomenon is depicted in FIG. 11 by the appearance of levels of temperature increase corresponding to parts of the square wave signal S in which power is injected into the heating element.

The temperature deviation between the temperature measured at the level ($T_2$) and the temperature measured in the absence of fouling ($T_1$) is representative of the fouling formed at the instant corresponding to the measurements that have been taken and more especially of the thickness of the fouling layer.

This thickness is obtained by formulas that are well known to one skilled in the art and that depend on the geometrical configuration of the sensor, i.e., a flat geometry for the sensor 10 of FIG. 1.

More generally, the thickness of the fouling layer is given by the following equation:

$$\frac{P}{2 \cdot D^2 \cdot h} + \frac{P \cdot e}{2 \cdot \lambda} + T_1 - T_2 = 0$$

where:

P, in W, designates the electrical output supplied to the heating element that corresponds essentially to the output generated by the heat flow, h, in W/m²/K, designates the coefficient of convective heat transfer, D, in m, designates the diameter of the heating element when the latter is of cylindrical shape or, in surface equivalence, the side of the heating element when the latter is of square shape, $T_1$ and $T_2$, in K, respectively designate the temperature measured in the no heating phase and the heating phase, λ, in W/m/K, designates the coefficient of thermal conductivity of the fouling layer that is deposited on the surface of the sensor, and finally, e, in m, designates the measured thickness of the fouling layer that is deposited on the surface of the sensor.

It should be noted that the more the thickness of the deposit formed on the sensor surface increases, the more the temperature rise will be significant for a given output.

In practice, the process calls for imposing a set heat value in output (example: 10 mW) by applying an electrical current whose intensity can vary from 0.1 to 10 mA, for determining the temperature deviation that results therefrom (increase), and then calculating the thickness of the fouling layer.

It should be noted that current compensation can be implemented depending on possible variations of the fluid temperature, for example by knowing the fluid temperature obtained during phases of no heating. Thus, the current that must be injected into the heating element to observe the set output value is determined.

It should be noted that the length of the heating period varies from several seconds to several minutes, as shown in FIGS. 10 and 11, where the elapsed time is expressed in seconds.

The length of the heating period is not necessarily equal to the length of no heating, but for practical reasons of implementing the invention, equal time intervals of heating and no heating will be preferred. Moreover, the length of the period of heating and/or no heating can vary over time in order to dynamically adapt to the operating conditions of the industrial process, but, in practice, an optimum length will be determined, fixed and maintained according to the application and the industrial process.

From a practical standpoint, the temperature deviation $T_2-T_1$ is determined by using linear and/or nonlinear regression algorithms between two periods of no heating that surround a period of heating.

It should be noted that an upper limit of supply output can be provided in the regulation phase so that in case of no fouling, the output necessary to generate the desired temperature deviation does not exceed the physical output limit of the electronic system.

It should be noted that the simple detection of a significant temperature deviation, such as, for example, a deviation of 1 degree Celsius, provides significant information since it is representative of fouling that has formed within a container that contains a fluid.

Such information can, for example, lead to sending an alarm signal for the purpose of warning an operator or maintenance personnel of the installation.

This detection function can, of course, be linked to the function of measuring the fouling in order to be able equally to provide quantitative information on the thickness of the fouling layer that has thus formed.

Based on microsystem processes and technologies, the temperature measuring element has very high sensitivity and precision in temperature that is, for example, better than 0.05° C.

Moreover, these processes and technologies make it possible to design a sensor that has the following advantages and characteristics:

Small dimensions (proximity of the functional elements relative to one another), Low consumption, Capacity to generate low heat flows from the heating element, High sensitivity of the measuring element, Very short response times.

It thus becomes possible to measure fouling thicknesses with a zero fluid flow rate and with a fouling measurement sensitivity of around 1 µm. It should, moreover, be noted that the sensor illustrated in FIG. 9 is more sensitive than the one of FIG. 8 since it is in direct contact with the fluid.

Figure 12:
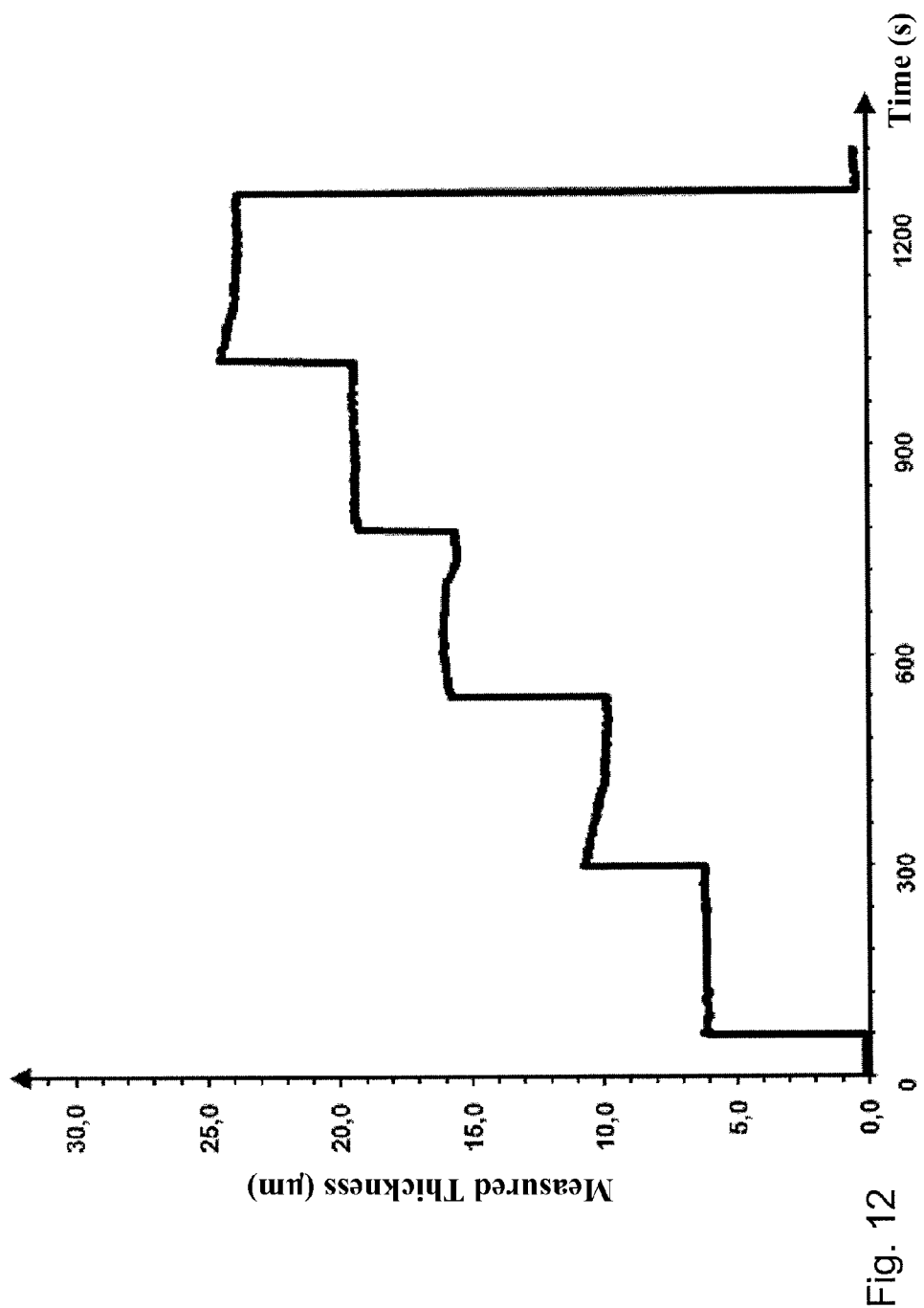
FIG. 12 schematically illustrates the progression of a curve of fouling formed on the sensor shown in FIGS. 2f and 9 over time.

FIG. 12 shows a curve of measurement of the fouling thickness obtained by implementing in succession, over time, deposits on the active outside surface of a sensor according to the invention, and by using a polymer resin spray whose heat conductivity is known. This curve was obtained in the laboratory, but under operating conditions similar to those of industrial applications such as a cooling circuit, for example.

The sensor that is used is the one shown in FIGS. 2f and 9 with the arrangement of the heating and measuring elements of FIG. 5a.

The heating element (layer 14) is formed from a Ti/Pt bilayer with a 500 Å thickness for the first layer and a 2000 Å thickness for the second. The insulating layer 44 is made of $Si_3N_4$.

The measuring element (layer 16) is formed from a Ti/Pt bilayer with a 500 Å thickness for the first layer and a 3000 Å thickness for the second. The insulating layer 46 is made of $Si_3N_4$.

The interface element (layer 18) is formed from a Ti/Au bilayer with a 500 Å thickness for the first layer and a 1000 Å thickness for the second.

The experimental method consists in taking a first series of measurements with the sensor without any deposit on its surface (calibration phase).

Then, a first polymer resin deposit is made on the surface of the layer 18 of the sensor, baking at 100° C. for 60 seconds is done to harden the resin, and a series of measurements of thickness is taken with the sensor connected to its electronic measurement system.

The first level of the curve is thus obtained.

Thus, four other successive deposits with one measurement of thickness each time are implemented, thus yielding four other levels.

It should be noted that the successive deposits do not follow a linear increase due to successive bakings that have been undergone by the layers formed in the preceding stage. It is found that the measured thicknesses are on the order of several micrometers; this shows the great sensitivity of the sensor.

The sensors of the aforementioned embodiments can be used according to two operating methods, of which the first has already been presented above, and they will be taken up again more generally below.

A first method (first embodiment of the process according to the invention) consists in using square waves that are periodic in time such as are shown in FIGS. 10 and 11 (typically from 30 s to several minutes) in order to regularly heat the heating element and to have rest periods. Since the temperature is being continuously measured and provided by the unit 26, this temperature is the temperature of the fluid in a rest period (identified by T1 in FIGS. 10 and 11). In a heating period, this measured temperature is stabilized at the value T2 that is the skin temperature (or wall temperature) resulting from heat transfer from the heating element toward the medium to be measured across the interface element (or directly when there is no interface element) and, potentially, across a fouling layer.

In the absence of fouling, the wall temperature (in the heating phase) is equal to the fluid temperature (to measurement errors near and according to the heat resistance generated by the thickness of the interface element 18 when it is present) because the totality of the heat flow is dissipated into the measurement medium.

In the presence of fouling, an additional heat resistance opposes heat transfer toward the measurement medium, and the skin temperature (T2) assumes a value of greater than T1.

Thus, the fluid temperature (T1) and the skin temperature (T2) are properly known. To determine the thickness of the fouling, the aforementioned formulas and equations are applied so as to provide information to the display 28 (typically, the thickness of the fouling and the fluid temperature) and/or to the transmitter 30 in order to deliver a standardized signal (typically, 4-20 mA) to be integrated into a monitoring or a signal recorder.

Thus, advantageously, according to this method, the thickness of the fouling forming on the surface of the measuring device (sensor) is continuously evaluated in order to supply information to the user on the state of cleanliness.

This method does not require either preliminary calibration of the measurement device according to the conditions of use (flow rate or nature of the fluid) or a posteriori processing of information to determine the thickness of fouling. On the other hand, variations of operating conditions (within a certain limit, such as the temperature, the flow rate, the pressure) do not influence the measurement of fouling (this imparts high reliability to the method and allows continuous use and application in industrial environments) since the device regularly recalculates the fluid temperature.

Finally, if the nature of the fouling that is forming is known a priori and its heat conduction is known a fortiori, the system can then supply a signal of the thickness of fouling in µm or mm units; if not, the system bases itself on a default value of heat conduction from the fouling layer that can form, and the measurement signal is ultimately an indicator according to an arbitrary unit.

According to a second method (second embodiment of the measuring process according to the invention), instead of using cycles of heating and no heating phases repeated indefinitely to know the temperature of the fluid (obtained in the no heating phase), constant heating can be initiated on the condition of:

Either being in an application case in which the temperature does not vary, or then does not vary when measurements are desired to be taken, in which case the temperature is known and can be known from the unit 26 (T1 is thus fixed), Or the temperature is variable, but there are other means available for knowing this temperature (via a second temperature sensor already present, whose data reach the unit 26 or that can be easily derived by one skilled in the art in the existing device), in which case the temperature T1 is provided continuously.

The constant heating of the device allows information to be obtained more dynamically about the thickness of the fouling based on the difference T2−T1, or more or less real time information regarding the kinetics of formation and disappearance by treatment of the fouling (typically less than 0.5 s).

Thus, this operating mode makes it possible to track rapid phenomena of increase or decrease of fouling such as the tracking of cleaning phases in the agricultural industry, for example. This is therefore useful for optimizing these cleaning phases (often long and always expensive), knowing that no real device (nor any global method) can track the effectiveness of these cleanings in real time.

It should be noted that the first method could, however, be used to track the phases of cleaning in industries in which the time constraint is less critical.

The invention claimed is:

1. A sensor for measuring and/or detecting the fouling that forms directly or indirectly on a front surface of the sensor that is exposed to fluid, wherein the sensor comprises the following in the form of a plurality of superimposed layers:
   at least one heating element that is able to diffuse, on command, a homogenous, monitored heat flow whose heat output is essentially less than 200 mW,
   a heat insulator located on a side opposite the front surface of the sensor to prevent dissipation of the heat flow from said opposite side,
   at least one temperature measuring element that is placed in the homogenous heat flow diffused by said at least one heating element and that offers a precision of temperature measurement of better than 0.1° C., and
   a substrate on which the layers of said at least one heating element and at least one temperature measuring element are connected, wherein the substrate has opposite first and second surfaces, the heat insulator facing the first surface and the layer of said at least one heating element facing the second surface, the layer of said at least one temperature measuring element being superimposed on the layer of said at least one heating element.

2. The sensor according to claim 1, wherein said at least one temperature measuring element has a surface area that is at least less than 2% of the surface area of an active surface of said at least one heating element.

3. The sensor according to claim 1, wherein said at least one heating element has an active surface with a surface area of less than or equal to 25 mm$^2$.

4. The sensor according to claim 1, wherein said at least one temperature measuring element has an active surface with a surface area of less than or equal to 0.49 mm$^2$.

5. The sensor according to claim 1, wherein said at least one heating element has a size that is less than or equal to 25 mm$^2$.

6. The sensor according to claim 5, wherein said at least one heating element and said at least one temperature measuring element are each platinum resistors.

7. The sensor according to claim 1, comprising at least one heat-conductive interface element having opposite inside and outside surfaces, the inside surface being oriented toward said at least one measuring element and the outside surface being positioned to be in contact with the fluid.

8. The sensor according to claim 7, wherein said at least one interface element has a heat resistance that is less than or equal to 10° C./W.

9. The sensor according to claim 7, wherein said at least one interface element is made of stainless steel.

10. A system for measuring and/or detecting a fouling that has formed directly or indirectly on a front surface of a sensor that is exposed to a fluid, the sensor comprising the following in the form of superimposed layers:
    at least one heating element that is able to diffuse, on command, a homogenous, monitored heat flow,
    a heat insulator located on a side opposite the front surface of the sensor for preventing dissipation of the heat flow from said opposite side,
    at least one temperature measuring element that is placed in the homogenous heat flow diffused by said at least one heating element, and
    a substrate on which the layers of said at least one heating element and at least one temperature measuring element are connected, wherein the substrate has opposite first and second surfaces, the heat insulator facing the first surface and the layer of said at least one heating element facing the second surface, the layer of said at least one temperature measuring element being superimposed on the layer of said at least one heating element,
    the system comprising:
       means for determining a temperature deviation between, on the one hand, a wall temperature measured by said at least one temperature measuring element when said at least one heating element diffuses as a heat flow, and on the other hand, the temperature of the fluid, and
       means for calculating a thickness of the fouling formed on the front surface of the sensor exposed to the fluid based on the determined temperature deviation.

11. The system according to claim 10, wherein said at least one heating element generates a heat output that is less than 200 mW, and said at least one temperature measuring element offers measurement precision of better than 0.1° C.

12. A sensor for measuring and/or detecting the fouling that forms directly or indirectly on a front surface of the sensor that is exposed to fluid, wherein the sensor comprises the following in the form of a plurality of superimposed layers:
    at least one heating element that is able to diffuse, on command, a homogenous, monitored heat flow whose heat output is essentially less than 200 mW,
    a heat insulator located on a side opposite the front surface of the sensor to prevent dissipation of the heat flow from said opposite side,
    at least one temperature measuring element that is placed in the homogenous heat flow diffused by said at least one heating element and that offers a precision of temperature measurement of better than 0.1° C., and
    a substrate on which the layers of said at least one heating element and at least one temperature measuring element are connected, wherein the substrate has opposite first and second surfaces, the heat insulator facing the first surface, the layer of said at least one heating element being located between the heat insulator and the first surface of the substrate, and the layer of said at least one temperature measuring element being located facing the second surface of the substrate.

13. The sensor according to claim 12, wherein said at least one temperature measuring element has a surface area that is at least less than 2% of the surface area of an active surface of said at least one heating element.

14. The sensor according to claim 12, wherein said at least one heating element has an active surface with a surface area of less than or equal to 25 mm$^2$.

15. The sensor according to claim 12, wherein said at least one temperature measuring element has an active surface with a surface area of less than or equal to 0.49 mm$^2$.

16. The sensor according to claim 12, wherein said at least one heating element has a size that is less than or equal to 25 mm$^2$.

17. The sensor according to claim 16, wherein said at least one heating element and said at least one temperature measuring element are each platinum resistors.

18. The sensor according to claim 12, comprising at least one heat-conductive interface element having opposite inside and outside surfaces, the inside surface being oriented toward said at least one measuring element and the outside surface being positioned to be in contact with the fluid.

19. The sensor according to claim 18, wherein said at least one interface element has a heat resistance that is less than or equal to 10° C./W.

20. The sensor according to claim 18, wherein said at least one interface element is made of stainless steel.

21. A system for measuring and/or detecting a fouling that has formed directly or indirectly on a front surface of a sensor that is exposed to a fluid, the sensor comprising the following in the form of superimposed layers:
- at least one heating element that is able to diffuse, on command, a homogenous, monitored heat flow;
- a heat insulator located on a side opposite the front surface of the sensor for preventing dissipation of the heat flow from said opposite side;
- at least one temperature measuring element that is placed in the homogenous heat flow diffused by said at least one heating element; and
- a substrate on which the layers of said at least one heating element and at least one temperature measuring element are connected, wherein the substrate has opposite first and second surfaces, the heat insulator facing the first surface, the layer of said at least one heating element being located between the heat insulator and the first surface of the substrate, and the layer of said at least one temperature measuring element being located facing the second surface of the substrate, the system comprising:
- means for determining a temperature deviation between, on the one hand, a wall temperature measured by said at least one temperature measuring element when said at least one heating element diffuses as a heat flow, and on the other hand, the temperature of the fluid; and
- means for calculating a thickness of the fouling formed on the front surface of the sensor exposed to the fluid based on the determined temperature deviation.

22. The system according to claim 21, wherein said at least one heating element generates a heat output that is less than 200 mW, and said at least one temperature measuring element offers measurement precision of better than 0.1° C.

\* \* \* \* \*